United States Patent [19]

Rihova et al.

[11] Patent Number: 6,071,888
[45] Date of Patent: Jun. 6, 2000

[54] COMPOSITION FOR TREATING CANCER

[75] Inventors: Blanka Rihova, Prague, Czech Rep.; Yveta Germano, Alpharetta, Ga.; Olga Kufudaki, deceased, late of Prague, Czech Rep., by Alekos Kufudakis, legal representative

[73] Assignee: Aliatros Medical, a.s., Czech Rep.

[21] Appl. No.: 08/787,209

[22] Filed: Jan. 22, 1997

Related U.S. Application Data

[60] Provisional application No. 60/010,517, Jan. 24, 1996.
[51] Int. Cl.⁷ .......................... A01N 43/04; A01N 43/08; A01N 37/34
[52] U.S. Cl. .............. 514/43; 514/23; 514/527; 514/474
[58] Field of Search .................. 514/53, 276, 356, 514/474, 561, 527

[56] References Cited

U.S. PATENT DOCUMENTS 4,582,807  4/1986  Veeraraghavan .

*Primary Examiner*—Lila Feisee
*Assistant Examiner*—Lin Sun-Hoffman
*Attorney, Agent, or Firm*—Bruce Jacobs

[57] ABSTRACT

The present invention is directed to compositions containing beta-alanine which are useful for treating cancer. The composition preferably comprises a ribose compound, L-beta-alanine, ascorbic acid, and nicotinic acid. The present invention is particularly directed to a composition useful for treating melanoma, and a method for treating melanoma with the composition.

11 Claims, 4 Drawing Sheets

COMPOSITION FOR TREATING CANCER

CROSS REFERENCE TO RELATED APPLICATION

This application claims the benefit of U.S. Provisional Application Ser. No. 60/010,517 filed Jan. 24, 1996.

FIELD OF THE INVENTION

The present invention is directed to a composition useful for treating cancer, particularly melanoma.

BACKGROUND OF THE INVENTION

Cancer afflicts many individuals each year. Melanoma tumors, for instance, originate from melanocytes, pigment cells that are normally present in the epidermis and sometimes in the dermis. Melanoma affects about 28,000 individuals yearly in the United States, and kills about 5,800 of these individuals. Melanoma incidence has increased dramatically (700% in the last 40 years). If the incidence continues to increase at the present rate, risk of melanoma will approximate about 1 percent within a decade lifetime.

Immunomodulating compositions have been designed to treat various immunodeficiencies and autoimmunological disorders. Ongoing research continues to evaluate whether these compositions may be useful in treating one or more malignant diseases.

Greek Patent Specification No. 72,440 discloses an immunomodulating composition containing a mixture of D-ribose, DL-alpha alanine, nicotinic acid and ascorbic acid. The composition is asserted to have a pronounced immunomodulating activity and to be able to rebuild the metabolic equilibrium and strengthen the immunity of an affected mammal.

PCT application CZ94/00015, filed Jul. 12, 1994, discloses an improvement upon the composition of the Greek patent and incorporates 2-deoxy-D-ribose, thiamin, and glutamic acid amide therein. The resulting improved composition has been found useful in immunomodulating and adjuvant therapy in combination with a metabolic stressor.

It has now been unexpectedly discovered that similar compositions in which the DL-alpha alanine is replaced with L-beta-alanine significantly enhance a mammal's resistance to cancer, particularly to melanoma.

It is an object of this invention to produce a composition capable of enhancing a mammal's resistance to cancer and prolonging the mammal's life.

It is a further object of this invention to treat a mammal inflicted with cancer by causing the composition to enter the blood stream of the mammal.

SUMMARY OF THE INVENTION

The present invention is directed to compositions containing beta-alanine which are useful for treating cancer. The composition preferably comprises a ribose compound, L-beta-alanine, ascorbic acid, and nicotinic acid. More preferably the composition is administered in a sodium chloride (saline) solution. The present invention is also directed to a method for treating cancer tumors in mammals by introducing the ingredients of the composition into the blood stream of the mammal. The present invention is particularly directed to a composition useful for treating melanoma, and a method for treating melanoma with the composition.

DESCRIPTION OF THE PREFERRED EMBODIMENTS

Figure 1:
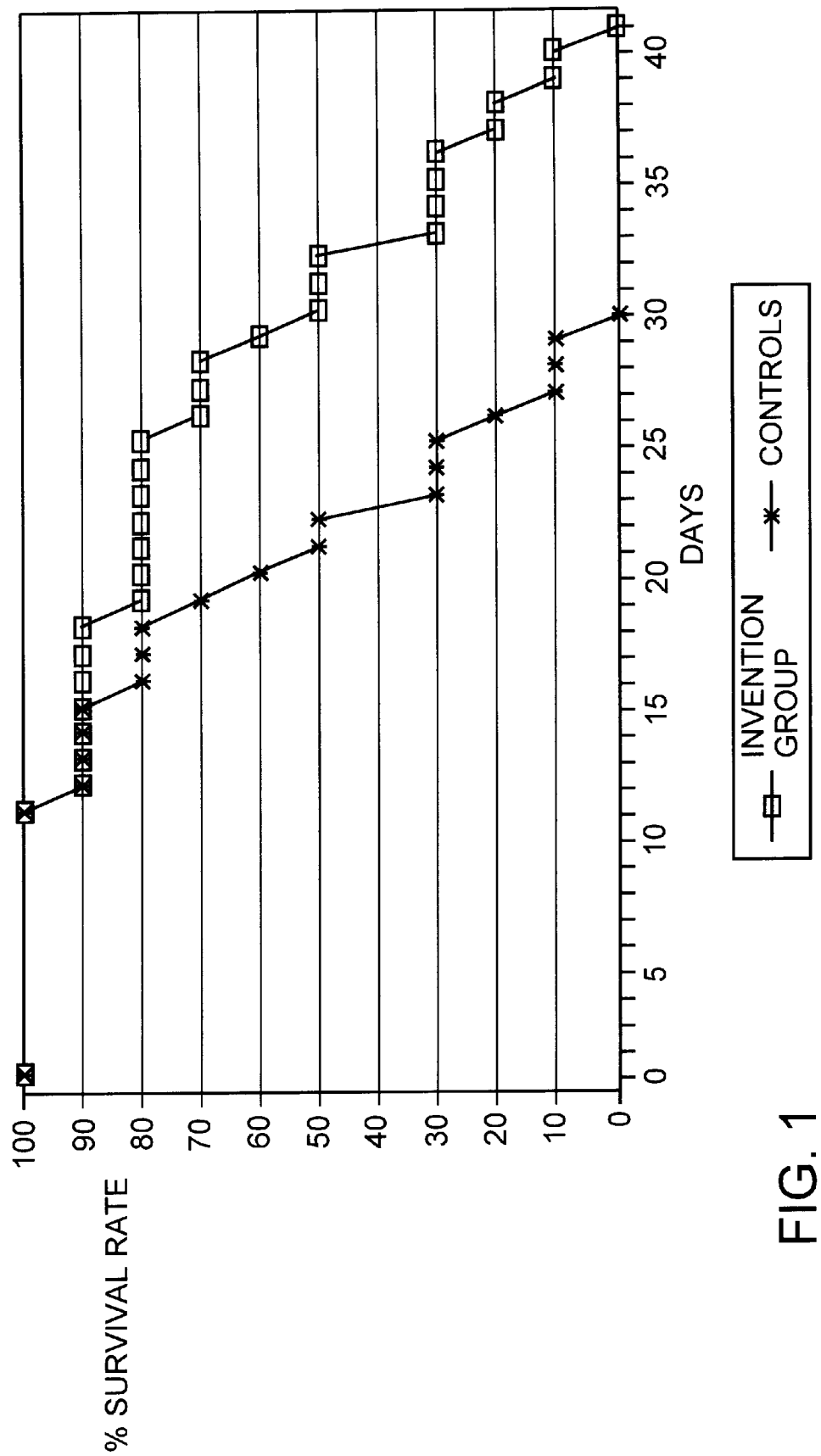
FIG. 1 is a graph showing the mice survival rate of melanoma-inflicted mice treated with this invention, and untreated melanoma-inflicted mice.

The present invention is directed to compositions containing beta-alanine and the use thereof in the treatment of cancer. Preferably the compositions comprise a ribose compound, L-beta-alanine, ascorbic acid, and nicotinic acid. The present invention is also directed to a method for treating cancer tumors in mammals with the composition. The present invention is preferably directed to a composition for treating melanoma, and a method for treating melanoma with the composition. A preferable delivery means for intravenous administration of the composition is a sodium chloride (saline) solution. Animal studies indicate that the composition generally prolongs the life of a mammal afflicted with a melanoma by at least about 25% and preferably by as much as 100%, as compared to a mammal with the same melanoma that does not receive any treatment.

Suitable ribose compounds for use herein include, but are not limited to, ribose, deoxyribose (2-deoxy-D-ribose), other ribose derivatives, and mixtures thereof. The ribose compounds and all other ingredients of the composition are known materials and can be obtained from manufacturers such as Sigma Aldrich and Merck.

The ribose compound is generally present in the composition in an amount that is at least about 30 wt %, preferably between about 30 to about 50 wt %, more preferably between about 35 to about 45 wt %, and even more preferably between about 38 to about 42 wt %, based upon the total weight of the composition. A suitable amount of the beta-alanine is generally at least about 1 wt %, preferably less than about 1 to about 45 wt %, more preferably between about 5 to 25 wt %, and more preferably between 8 to about 15 wt %, based upon the total weight of the composition. Ascorbic acid is generally present in an amount of at least 10 wt %, preferably between about 10 to 30 wt %, and more preferably between about 15 to about 25 wt %, based upon the total weight of the composition. Nicotinic acid is generally present in an amount of at least 1 wt %, preferably at least about 1 to about 20 wt %, and more preferably from about 5 to about 12 wt %, based upon the total weight of the composition. Other ranges within the ranges expressly mentioned above may be suitable.

The composition of this invention may be prepared by mixing the ribose compound, beta-alanine, ascorbic acid, and nicotinic acid in a sodium chloride (saline) solution. The ingredients may be mixed conventionally, i.e. by stirring, until a substantially homogenous mixture is obtained. The mixing time required to form the homogenous mixture depends on factors such as the temperature, the degree of mixing, and the like. The mixing temperature is preferably about room temperature, but is not critical provided that none of the ingredients are harmed by exposure to heat.

A blended composition containing all of the ingredients of the present composition has been found to have a storage stability of up to about 6 months. To provide enhanced stability, it is preferable that the composition be in the form of two premixtures. Thus, the composition is preferably prepared by (i) forming a first pre-mixture of ascorbic acid, ribose compound, water, and sodium chloride; (ii) forming a second pre-mixture of beta-alanine, nicotinic acid, water, and sodium chloride; and (iii) combining the two pre-mixtures prior to delivery to the mammal. Generally, the pre-mixtures will be kept separate until shortly prior to administration, i.e. within a few months. Although not currently recommended, it may be possible to administer the two premixtures sequentially.

The cancer-treating compositions may also contain other compounds advantageous to the metabolic activity of cells. For example, adenosine triphosphate-forming compounds may be added, e.g. nicotinic acid derivatives or precursors. Suitable such nicotinic acid derivatives include nicotinamide adenine dinucleotide (NAD), hydronicotinamide adenine dinucleotide (NADH), and nicotinamide adenine dinucleotide phosphate (NADP). Adenosine monophosphate may be used as a precursor to NAD. Other adenosine compounds may be used. Such compounds may be present in the composition in an amount of at least 5 wt %, and preferably between about 5 to about 50 wt %, based upon the total weight of the composition. Other ranges within the ranges expressly mentioned above may be suitable.

Further, the composition may contain stabilizers, e.g. $NaHCO_3$, to increase the pH of the composition.

The composition is preferably administered to a mammal intravenously, but may also be administered in the form of capsules, tablets, powders, drinking liquids, suppositories, and the like. The composition may also be administered intratumorally, intraperitonially, and topically.

The mechanism by which the composition of the present invention prolongs the lives of cancer-inflicted mammals has not been determined, and Applicant does not wish to be bound by any theory. However, evidence suggests that the composition stimulates (i) endogenous immune reactions including the mammal's ability to synthesize cytokines, and (ii) primary and secondary immune responses. The compositions may also directly inhibit tumor growth. Evidence also suggests that the beta-alanine forms stronger bonds with other components of the composition, i.e. nicotinic and ascorbic acids, as compared to the alpha-alanine of the prior art.

The invention is illustrated in the following nonlimiting examples. All parts and per cents are by weight unless otherwise specified.

EXAMPLE 1

A composition of this invention (currently referred to as Deranin B by Applicant) was prepared as follows.

A first pre-mixture was formed using a mixer equipped with a stirrer and a source of nitrogen. The mixer was filled with 5 ml water and sterile nitrogen was bubbled through the water for about 20 minutes. During the nitrogen bubbling, 300 mg of 2-deoxy-D-ribose was added and mixed into the water. Then, 45 mg sodium chloride, and 150 mg ascorbic acid were dissolved in the water. No direct sunlight contacted the mixture, and the resulting first pre-mixture solution was sterilized by passing it through a membrane filter. The solution was placed into a 5 cc vial under nitrogen in an aseptic environment.

A second pre-mixture was prepared by mixing 50 mg nicotinic acid, 5 ml water, and 45 mg sodium chloride, and 80 mg of L-beta-alanine in the same manner as the first pre-mixture. The second pre-mixture was also filtered through a membrane filter and the solution was placed in a 5 cc vial and sealed. The sealed vial was sterilized in an autoclave for about 20 minutes at 120° C.

The first and the second pre-mixtures were then mixed together to form the treatment composition between about 1 and 6 hours prior to intravenous administration.

EXAMPLE 2

To evaluate the effectiveness of the composition of Example 1 in prolonging the life of mammals afflicted with melanoma, 20 inbred female mice having body weights of about 18–20 grams were divided into an experimental group and a control group of 10 animals each. Each of the experimental group and control group animals were subcutaneously administered with about two million tumor cells of melanoma B16 to induce melanoma tumors in the mice.

About 0.05 ml/20 g body weight of the treatment composition as prepared in Example 1 was administered intravenously to each mouse in the experimental group about 24 hours after administration of the melanoma B16. Thereafter, additional doses of the composition were prepared and administered intravenously, at the same dosage rate, for each of the next 5 days, i.e. during the first week. During the second to fifth weeks, additional amounts of the composition were administered to the experimental animals twice a week, i.e. for a total of 14 treatments.

Figure 2:
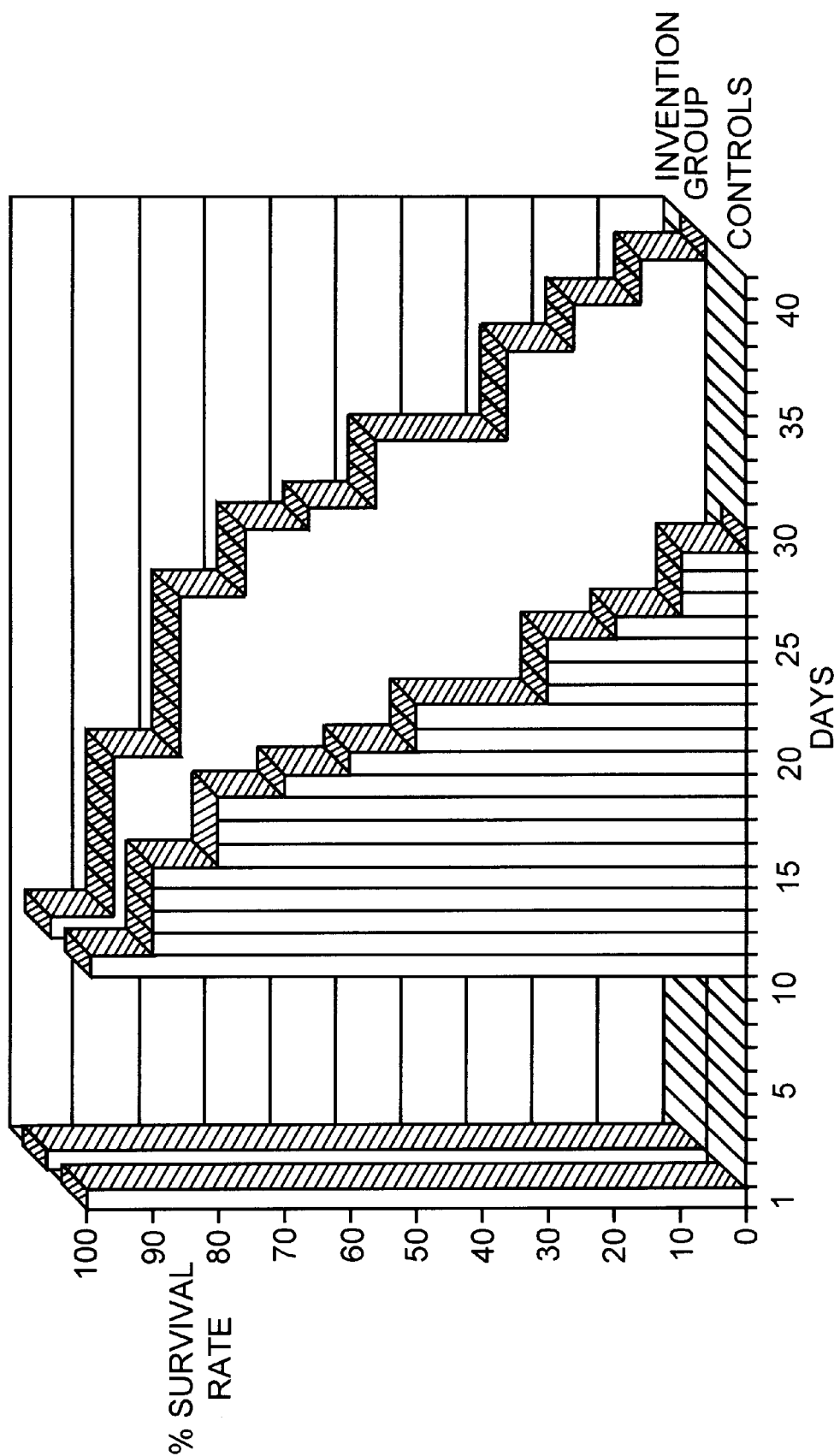
FIG. 2 is a three-dimensional graph showing the mice survival rate of melanoma-inflicted mice treated with this invention, and untreated melanoma-inflicted mice.

Table 1 identifies the number of days before the last of the mice in the experimental group and the control group died. Treatment with the beta-alanine containing composition prolonged the mice group survival by 11 days as compared to the untreated control group. FIGS. 1 and 2 provide a breakdown of the mice survival of the melanoma-inflicted mice in both the experimental and control groups. As can be seen in the Figures, at the 30th day when all of the mice in the control group had died, 11 (55%) of the treated mice remained alive. 50% of the mice in the control group died by the 22nd day. 50% of the mice in the experimental group lived until the 32nd day.

TABLE 1

| GROUP | MICE SURVIVAL |
| --- | --- |
| Experimental (beta-alanine) | 41 days |
| Control (untreated) | 30 days |

COMPARATIVE EXAMPLE A

For comparison purposes, the procedure of Example 2 was repeated with the exception that a prior art composition (in which the L-beta-alanine was replaced with the DL-alpha-alanine) was used. The data presented in Table 2 shows that mice treated with the alpha-alanine prior art composition lived only a few days longer than the mice in the untreated control group. Specifically Table 2 indicates that the mice treated with the prior art alpha alanine-containing composition survived only 3 days more than the mice in the control group.

TABLE 2

| GROUP | MICE SURVIVAL |
| --- | --- |
| Experimental (beta-alanine) | 41 days |
| Comparative Example (alpha alanine) | 33 days |
| Control (no treatment) | 30 days |

The treatment composition of this invention significantly prolongs the life of mice afflicted with melanoma as compared to mice treated with an identical composition in which the beta-alanine is replaced by alpha-alanine.

EXAMPLE 3

In this Example, a treatment composition was prepared according to the procedure of Example 1 except that 80 mg of adenosine-5'-monophosphate disodium salt was added to the composition of the second pre-mixture.

To evaluate the effectiveness of this composition in prolonging the life of mammals afflicted with melanoma, 50 inbred female mice weighing about 18–20 grams each were divided into one experimental group of 40 mice and a control group of 10 mice. The group of 40 mammals was divided into four subgroups with 10 mice in each subgroup. To induce melanoma tumors in the mice, all 50 mice were subcutaneously administered with about two million tumor cells of melanoma B16.

Thereafter, about 0.05 ml of the treatment composition was administered twice (once intravenously in the morning and once intraperitonially in the afternoon). In subgroup A, the treatment composition was administered 3 days after tumor inducement. In subgroup B, the treatment composition was administered 5 days after tumor inducement. In subgroup C, the treatment composition was administered 7 days after tumor inducement. In subgroup D, the treatment composition was administered 10 days after tumor inducement.

In all subgroups the primary melanoma tumors which formed were surgically removed 10 days after tumor inducement (leaving only metastatic tumors). For subgroup D, the primary melanoma tumor was removed prior to first administration of the treatment composition.

The mice in the control group were administered a physiological solution daily from the 10th day after tumor inducement until the last mouse died on the 32 day after tumor inducement.

Table 3 identifies the number of days before the last of the mice in each subgroup and control group died.

TABLE 3

| SUBGROUP | MICE SURVIVAL |
| --- | --- |
| A | more than 100 days |
| B | more than 100 days |
| C | more than 100 days |
| D | 83 days |
| Control Group | 32 days |

As Table 3 indicates, the treatment composition whether administered at 3, 5, 7, or 10 days after melanoma tumor inducement substantially prolonged the life of the mammals. Specifically, the treatment composition administered 3, 5, or 7 days after tumor inducement resulted in mice living more than 300% longer than the longest-living mouse in the control group. The mice receiving treatment composition administered 10 days after tumor inducement lived more than 250% longer than the longest-living control group mouse.

The average survival periods of the mice in each subgroup and control group were calculated on the 50th and 100th day after tumor inducement. The results are shown in Table 4.

TABLE 4

|  | A | B | C | D |
| --- | --- | --- | --- | --- |
| 50 days | 42.7 | 42.7 | 38.6 | 34.1 |
| 100 days | 57.4 | 58.8 | 56 | 46.3 |
| Control | 24.5 | 24.5 | 24.5 | 24.5 |

As Table 4 indicates, the average survival period of mice treated at 3 days was 74 and 134% longer than the average survival period of the control group mice, when calculated at 50 and 100 days after tumor inducement. Similarly, the average survival period of mice treated at 5 days was 74 and 140% longer than the average survival period of the mice in the control group. The average survival period after 50 and 100 days for mice treated at 7 days after tumor induction was 58 and 129% longer than the average survival period of mice in the control group. The average survival period for mice treated at 10 days after tumor induction was 39 and 89% percent longer than the average survival period of the control group mice.

The results suggest that the composition is highly effective in treating cancer in mice and may also be effective in treating cancer in other mammals including humans.

EXAMPLE 4

The procedure of Example 3 was repeated except that the composition did not contain any adenosine-5'-monophosphate disodium salt. Table 5 identifies the number of days before the last of the mice in the subgroups and the control group died.

TABLE 5

| SUBGROUP | MICE SURVIVAL |
| --- | --- |
| A | more than 100 days |
| B | more than 100 days |
| C | more than 100 days |
| D | 51 days |
| Control Group | 32 days |

Table 5 indicates that the treatment composition, whether administered at 3, 5, 7 or 10 days after melanoma tumor inducement, substantially prolonged the life of the mammals.

The average survival periods of the mice in each subgroup and control group were calculated on the 50th and 100th day after tumor inducement. Table 6 shows the average survival period of the mice in subgroups A, B, C and D.

TABLE 6

|  | A | B | C | D |
| --- | --- | --- | --- | --- |
| 50 days | 37.5 | 37.3 | 33.7 | 33.5 |
| 100 days | 42.5 | 47.5 | 43.7 | 33.6 |
| Control | 24.5 | 24.5 | 24.5 | 24.5 |

These results suggest that the composition is highly effective in treating cancer in mice and may also be effective in treating cancer in other mammals including humans.

COMPARATIVE EXAMPLE B

In this Comparative Example, the procedure of Example 4 was repeated with the exception that the mammals were treated with a composition made from 80 mg D,L-alpha alanine, 150 mg D-ribose, 150 mg 2-deoxy-D-ribose, 150 mg ascorbic acid, 50 mg nicotinic acid, 10 ml water and 90 mg sodium chloride, i.e. a composition disclosed in PCT application CZ94/00015 and allowed U.S. Patent Application U.S. Ser. No. 08/564,328, the U.S. equivalent to PCT application CZ94/00 015.

Table 7 identifies the number of days before the last of the mammals in the experimental subgroup and the control group dies.

TABLE 7

| SUBCONTROL GROUP | MICE SURVIVAL |
| --- | --- |
| A | 51 days |
| B | 50 days |
| C | 41 days |
| D | 35 days |
| Control | 32 days |

Table 7 indicates that the treatment composition administered at 3, 5, 7, or 10 days after melanoma tumor inducement did not prolong the life of the mammals to the extent that the mammals with the compositions of the present invention in Examples 3 and 4 above.

The average survival periods of the mice in each subgroup and control group were calculated on the 50th and 100th day after tumor inducement. Table 8 shows the average survival period (in days) of the mice in subgroups A, B, C and D.

TABLE 8

|  | A | B | C | D |
| --- | --- | --- | --- | --- |
| 50 days | 30.9 | 29.9 | 28.8 | 27.8 |
| 100 days | 30.9 | 29.9 | 28.8 | 27.8 |
| Control | 24.5 | 24.5 | 24.5 | 24.5 |

Figure 3:
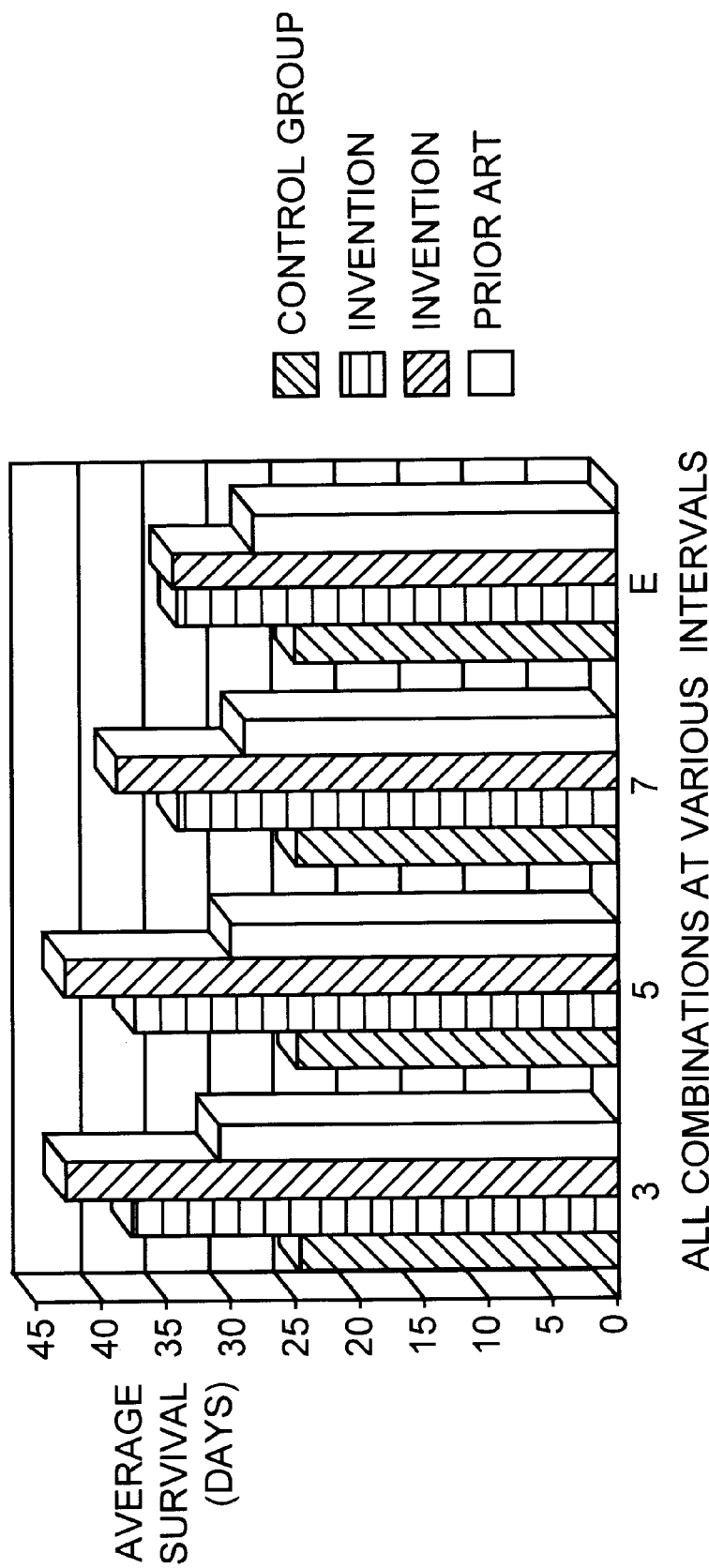
FIG. 3 is a three-dimensional graph showing the average mice survival rate at 50 days after tumor inducement of melanoma-inflicted mice treated with a composition of this invention at 3, 5, 7 and 10 days after tumor inducement (and untreated melanoma-inflicted mice).
Figure 4:
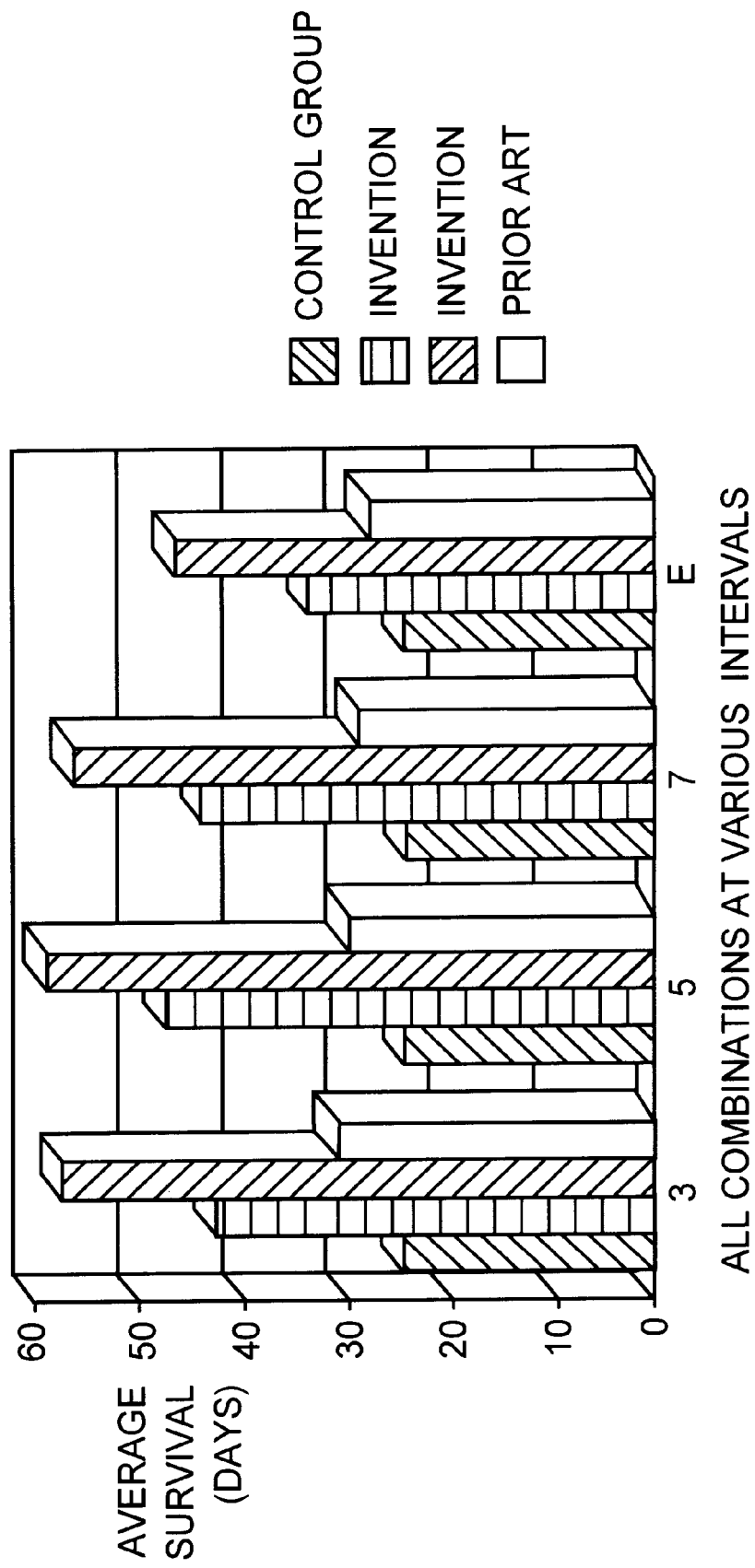
FIG. 4 is a three-dimensional graph showing the average mice survival rate at 100 days after tumor inducement of melanoma-inflicted mice treated with a composition of this invention at 3, 5, 7 and 10 days after tumor inducement (and untreated melanoma-inflicted mice).

FIGS. 3 and 4 are three-dimensional graphs that summarize the average survival period from Examples 3, 4, and Comparative Example B.

The data of this Comparative Example and Examples 3 and 4 indicate that the treatment composition of the present invention prolonged the life of mice afflicted with melanoma as compared to mice treated with the alpha-alanine-containing compositions of PCT application CZ94/00015.

What is claimed is:

1. A composition comprising a ribose compound selected from the group consisting of ribose, deoxyribose (2-deoxy-D-ribose), and mixtures thereof, beta-alanine, ascorbic acid, and nicotinic acid, wherein the ribose compound is present in an amount ranging from about 30 to about 50 wt %, based on the total weight of the composition.

2. The composition of claim 1, wherein the beta-alanine is present in an amount ranging from less than about 1 to about 45 wt %, based on the total weight of the composition.

3. The composition of claim 1, wherein the ascorbic acid is present in an amount ranging from about 10 to about 30 wt %, based on the total weight of the composition.

4. The composition of claim 1, wherein the nicotinic acid is present in an amount ranging from about 1 to about 20 wt %, based on the total weight of the composition.

5. The composition of claim 1, wherein the composition further comprises a compound selected from the group including adenosine triphosphate-forming compounds, nicotinic acid derivatives, nicotinic acid precursors, nicotinamide, adenine dinucleotide, hydronicotinamide adenine dinucleotide, nicotinamide adenine dinucleotide phosphate, adenosine monophosphate, and adenosine-5'-monophosphate disodium salt.

6. The composition of claim 5, wherein the additional compound is present in an amount ranging from about 5 to about 50 wt %, based on the total weight of the composition.

7. A composition made by combining a ribose compound selected from the group consisting of ribose, deoxyribose (2-deoxy-D-ribose), and mixtures thereof, beta-alanine, ascorbic acid, and nicotinic acid wherein the ribose compound is present in an amount ranging from about 30 to about 50 wt %, based on the total weight of the composition.

8. The composition of claim 7, wherein the beta-alanine is about 1 to about 45 wt % of the total weight of the composition.

9. The composition of claim 7, wherein the ascorbic acid is about 10 to about 30 wt % of the total weight of the composition.

10. The composition of claim 7, wherein the nicotinic acid is about 1 to about 20 wt % of the total weight of the composition.

11. The composition of claim 7, wherein the composition is made by further combining an additional compound selected from the group including adenosine triphosphate-forming compounds, nicotinic acid derivatives, nicotinic acid precursors, nicotinamide, adenine dinucleotide, hydronicotinamide adenine dinucleotide, nicotinamide adenine dinucleotide phosphate, adenosine monophosphate, and adenosine-5'-monophosphate disodium salt.

* * * * *